(12) United States Patent
Hamamoto et al.

(10) Patent No.: US 6,742,387 B2
(45) Date of Patent: Jun. 1, 2004

(54) CAPACITIVE HUMIDITY SENSOR

(75) Inventors: Kazuaki Hamamoto, Nagoya (JP); Inao Toyoda, Anjo (JP)

(73) Assignee: Denso Corporation, Kariya (JP)

(*) Notice: Subject to any disclaimer, the term of this patent is extended or adjusted under 35 U.S.C. 154(b) by 24 days.

(21) Appl. No.: 10/298,537

(22) Filed: Nov. 19, 2002

(65) Prior Publication Data

US 2003/0094045 A1 May 22, 2003

(30) Foreign Application Priority Data

Nov. 19, 2001 (JP) ........................ 2001-353606

(51) Int. Cl.⁷ ............ G01N 27/20; H01G 7/00; G01R 27/26
(52) U.S. Cl. ............ 73/335.04; 73/29.05; 361/286; 324/664
(58) Field of Search .............. 73/29.01, 29.05, 73/335.04; 361/286; 324/664

(56) References Cited

U.S. PATENT DOCUMENTS

| 4,263,576 A | * | 4/1981 | Murata et al. | ............ 338/35 |
|---|---|---|---|---|
| 4,429,343 A | * | 1/1984 | Freud | ............ 361/286 |
| 4,564,882 A | * | 1/1986 | Baxter et al. | ............ 361/286 |
| 4,898,476 A | * | 2/1990 | Herrmann et al. | ............ 374/28 |
| 4,926,156 A | * | 5/1990 | Dickert et al. | ............ 338/36 |

FOREIGN PATENT DOCUMENTS

| JP | 63-307346 | * 12/1988 | ............ 73/29.05 |
|---|---|---|---|
| JP | A-02-159547 | 6/1990 | ............ 73/335.04 |
| JP | A-03-18750 | 1/1991 | ............ 73/29.05 |

* cited by examiner

Primary Examiner—Daniel S. Larkin
(74) Attorney, Agent, or Firm—Posz & Bethards, PLC

(57) ABSTRACT

A capacitive humidity sensor includes a pair of opposed electrodes on a substrate. A humidity-sensitive film covers the electrodes. The electrodes are comb-shaped and interdigitated. Humidity is detected based on the capacitance between the pair of electrodes, which changes with changes according to the humidity in the atmosphere. The uniform width of each tooth in the pair of electrodes is L1, and the uniform distance between a tooth of one of the electrodes and a tooth of the other electrode is L2. When L1 is less than 3 micrometers, L2 is 5 micrometers. When L1 is greater than or equal to 3 micrometers, L2 is less than or equal to 5 micrometers.

1 Claim, 5 Drawing Sheets

CAPACITIVE HUMIDITY SENSOR

CROSS REFERENCES TO RELATED APPLICATIONS

This application relates to and incorporates by reference Japanese patent application no. 2001-353606, which was filed on Nov. 19, 2001.

BACKGROUND OF THE INVENTION

The present invention relates to a capacitive humidity sensor having a pair of comb-shaped electrodes on a surface of a substrate.

In a conventional capacitive humidity sensor, a lower electrode is formed on a substrate. A humidity-sensitive film, made of a polyimide material, the capacitance of which changes with humidity, is formed on the lower electrode. A thin, upper electrode, through which humidity can penetrate, is formed on top of the humidity-sensitive film. This type of device is called a vertically integrated sensor.

In this type of device, the lower electrode is formed on the substrate using a semiconductor process. Then the work piece is taken off of the semiconductor manufacturing line to deposit an organic humidity-sensitive film. Then the work piece is placed back on the semiconductor production line to form the top electrode. For this reason, the semiconductor production line is exposed to a risk of equipment contamination, requiring a special facility for forming the upper electrode. Therefore, the existing semiconductor production line cannot be used as is.

To address this issue, the inventors of the present invention have developed a capacitive humidity sensor, which is shown in FIG. 5. In this device, a pair of comb-shaped electrodes 31, 32 face each other and lie in the same plane, but are isolated from each other, on a surface of a substrate 10, so that the teeth of the comb-shaped electrodes are interdigitated. A humidity-sensitive film 50 is formed over the pair of comb-shaped electrodes 31, 32 and areas between the teeth of the comb-shaped electrodes that face each other. Humidity is detected based on a capacitance value between the pair of comb-shaped electrodes 31, 32, which changes in accordance with humidity changes in the atmosphere.

Such a device can be manufactured by forming the humidity-sensitive film 50 after the pair of comb-shaped electrodes 31, 32 are formed on a surface of the substrate 10, using a semiconductor process. Therefore, this device can be easily manufactured using an existing semiconductor production line.

The vertically integrated sensor mentioned earlier, however, makes effective use of the surface of the substrate, where the electrodes are formed. The sensor shown in FIG. 5, on the other hand, relies on surfaces at the edges of the electrode films.

For this reason, the distance along which the electrodes face each other in the sensor shown in FIG. 5 is smaller than in the vertically integrated sensor, when substrates of comparable sizes are used. As a result, the magnitudes of changes in the capacitance are smaller in the sensor shown in FIG. 5. In order to ensure changes in the capacitance sufficient for sensor output, a larger substrate surface would be required.

To address the issue described above, the objective of the present invention is to efficiently achieve relatively large capacitance changes in spite of a small substrate surface area.

The inventors have discovered that the capacitance changes by different magnitudes at different tooth widths of the comb-shaped electrodes. Also, the capacitance varies according to the spacing between the facing electrodes, or according to the spacing between the comb teeth, in the capacitive humidity sensor of FIG. 5.

The inventors performed experiments for achieving large capacitance changes, when the electrodes occupy a relatively small surface area, by optimizing the width of the electrodes and the spacing between the electrodes. The present invention has been made based on these experiments.

SUMMARY OF THE INVENTION

The present invention is a capacitive humidity sensor that includes a substrate; a pair of electrodes, which face each other on a surface of the substrate on the same plane but in isolation from each other; and a humidity-sensitive film, which covers the electrodes and an area between the electrodes. The comb-shaped electrodes have interdigitated teeth. Humidity is detected based on the capacitance between the pair of electrodes, which changes with changes according to the humidity in the atmosphere. The width of each tooth in the pair of electrodes is L1, and the distance between a tooth of one of the electrodes and a tooth of the other electrode, which face each other, is L2. When the width L1 is less than 3 $\mu$m, the distance L2 is 5 $\mu$m. When the width L1 is greater than or equal to 3 $\mu$m, the distance L2 is less than or equal to 5 $\mu$m.

DETAILED DESCRIPTION OF THE PREFERRED EMBODIMENT

Figure 1:
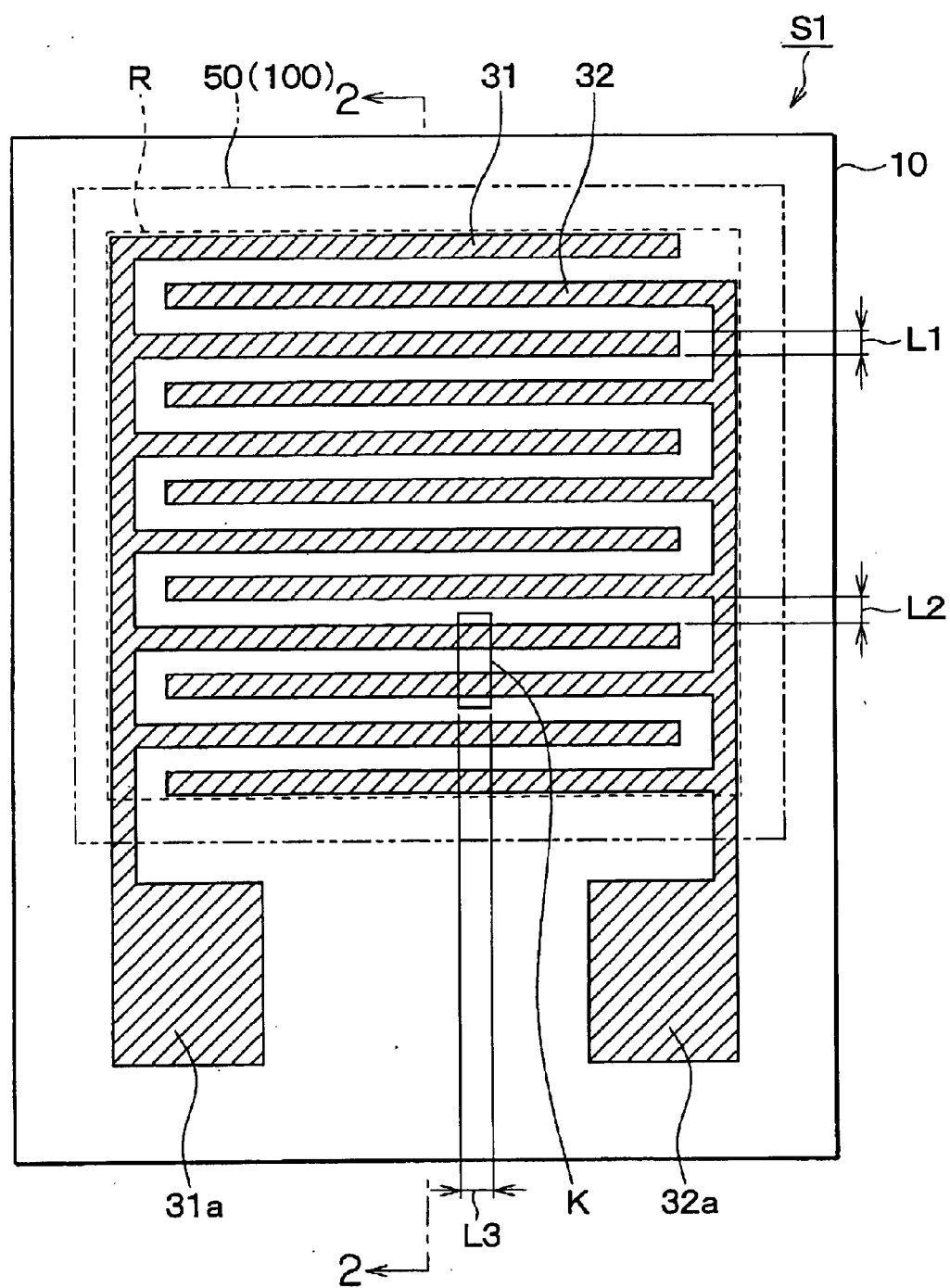
FIG. 1 is a plan view of the capacitive humidity sensor of one embodiment of the present invention.

The capacitive humidity sensor S1 of FIG. 1 may be used, for example, to facilitate humidity control for a room or vehicle air conditioner or to detect the humidity outdoors for weather observation. Incidentally, in FIG. 1, the diagonal shading lines are used for identifying a specific area and do not indicate a cross-section.

The semiconductor substrate 10 is, for example, a silicon substrate. A silicon oxide film 20, which is an insulating film, is formed on the semiconductor substrate 10. A pair of comb-shaped electrodes 31 and 32, which face each other, is formed on the silicon oxide film 20 in the same plane with each other but in isolation from each other.

Each of the comb-shaped electrodes 31, 32 has teeth, which are interdigitated and face each other. By adopting such a comb-shaped electrode structure, the electrodes have minimal areas while having maximized capacitance between the electrodes, because of the relatively long distance along which the electrodes 31, 32 face each other.

The electrodes 31, 32 may be formed with Al, Al—Si (in which a trace amount, for example, 0.x %, of Si is added to Al), Ti, Au, Cu, or polysilicon, all of which are regularly used on ordinary semiconductor production lines. In the present example, aluminum (Al) is used for the electrodes 31, 32.

A silicon nitride film 40, which is a passivation film, is formed over the pair of electrodes 31, 32. In the present example, the silicon nitride film 40 covers the electrodes 31, 32 and the area between the electrodes 31, 32. However, the silicon nitride film 40 only needs to cover the electrodes 31, 32 and does not necessarily need to cover the area between the electrodes 31, 32.

A humidity-sensitive film 50, the capacitance of which changes with humidity, is formed over the silicon nitride film 40 to cover both of the electrodes 31, 32 and the area between the electrodes 31, 32. In FIG. 1, the outer perimeter of the humidity-sensitive film 50 is shown with a broken line.

Figure 2:
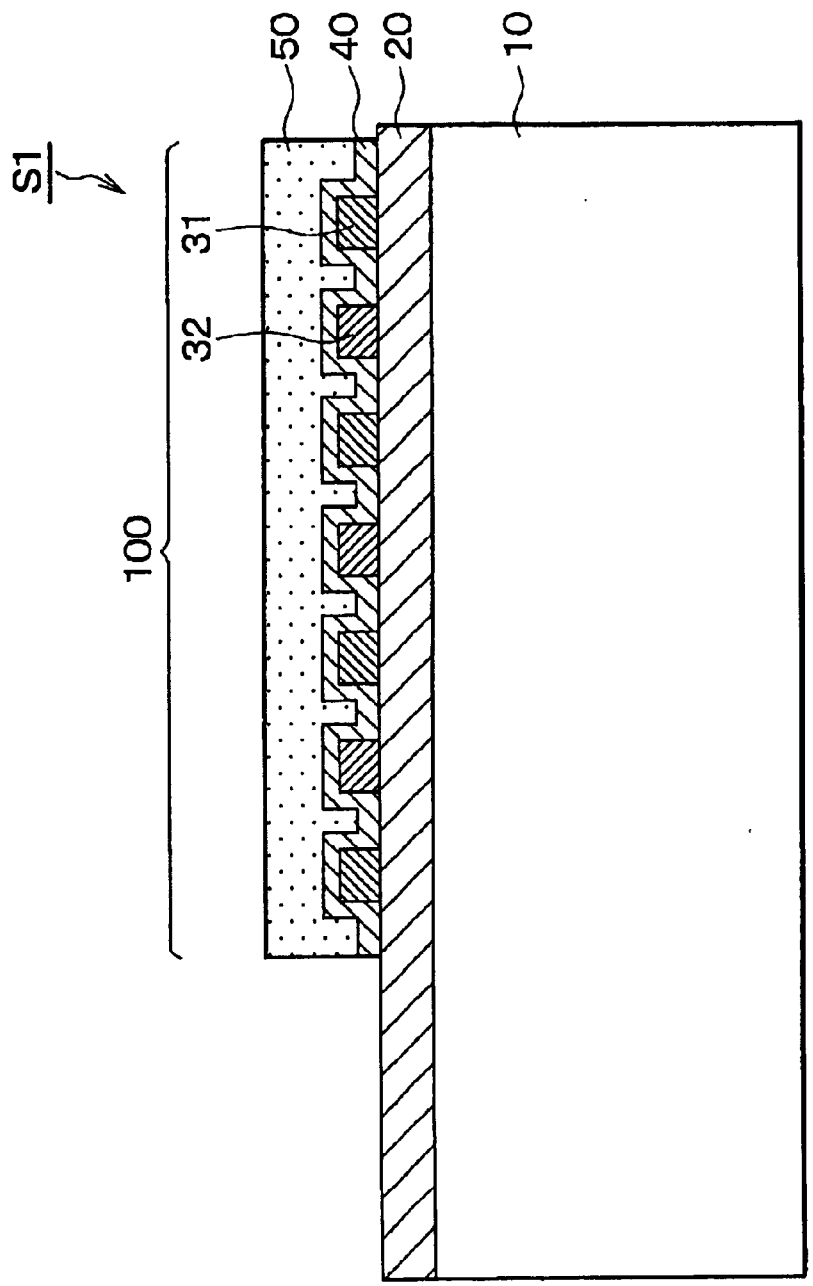
FIG. 2 is a cross-sectional diagram along a line 2—2 in FIG. 1.

In the present example, the humidity-sensitive film 50, that covers the area between the electrodes 31, 32 is deposited in low areas, below the top surfaces of the electrodes 31, 32, as shown in FIG. 2. In other words, the humidity-sensitive film 50 is formed in spaces between the electrodes 31, 32, across which the electrodes 31, 32 face each other.

A moisture absorbing organic polymer material may be used for the humidity-sensitive film 50, such as polyimide or butyric acid cellulose acetate. In the present example, the humidity-sensitive film 50 is made of polyimide.

When water molecules enter the humidity-sensitive film 50, the dielectric ratio of the film 50 changes. The dielectric ratio changes dramatically in proportion to the amount of moisture in the film, because water molecules have a large dielectric ratio. As a result, the capacitance between the electrodes 31, 32 also changes.

A humidity-sensitive area 100 is the area in which the humidity-sensitive film 50 is placed on the semiconductor substrate 10. Because the capacitance between the pair of electrodes 31, 32 changes with changes in humidity around the sensor S1, humidity detection is possible in the humidity-sensitive part 100 based on the changes in the capacitance.

Furthermore, as shown in FIG. 1, electrode pads 31a and 32a, for capturing signals corresponding to the changes in the capacitance values between the electrodes 31, 32, are electrically connected to the electrodes 31, 32 in an area outside of the humidity-sensitive part 100 on the surface of the semiconductor substrate 10, as shown in FIG. 1.

A method of manufacturing the capacitive humidity sensor S1 of the present example described above will be described next. Firstly, the silicon oxide film 20 is formed on the surface of the semiconductor substrate 10 by a thermal oxidation or CVD method.

Next, the electrodes 31, 32 for detecting the changes in humidity, as well as the electrode pads 31a and 32a, are formed by an Al sputtering or vapor phase deposition method and then are patterned. For example, the thickness of the electrodes 31, 32 might be approximately several tenths of micrometers. The silicon nitride film 40 is then deposited on top by a plasma CVD method.

Then, the humidity-sensitive film is formed, for example, by spin coating of a polyimide film, followed by curing and photoetching or by a printing step, followed by curing. The capacitive humidity sensor S1, shown in FIG. 1 and FIG. 2, can be manufactured using the manufacturing method described above on an ordinary semiconductor production line.

In the present embodiment, as shown in FIG. 1, L1 is used to represent the width of each tooth in the comb-shaped pair of electrodes 31, 32, and L2 represents the distance between a tooth of one of the electrodes and a tooth of the other electrode. When the width L1 is less than 3 μm, the distance L2 is 5 μm. When the width L1 is 3 μm or more, the distance L2 is 5 μm or less.

In other words, when L1>3 μm, L2<5 μm. When L1.3 μm, L2.5 μm. When these relationships are satisfied, the magnitude of changes in the capacitance can be maximized even when the substrate surface area is relatively small. As a result, the required changes in the capacitance can be effectively achieved while making the area of the substrate 10 occupied by the sensor S1 as small as possible.

A reason behind the relationship between the width L1 and the distance L2 for the pair of electrodes 31, 32, as described above, will be discussed next. In this discussion, L1 is the width of the electrodes L1, and the distance L2 is the size of the spacing between the electrodes L2.

Figure 3:
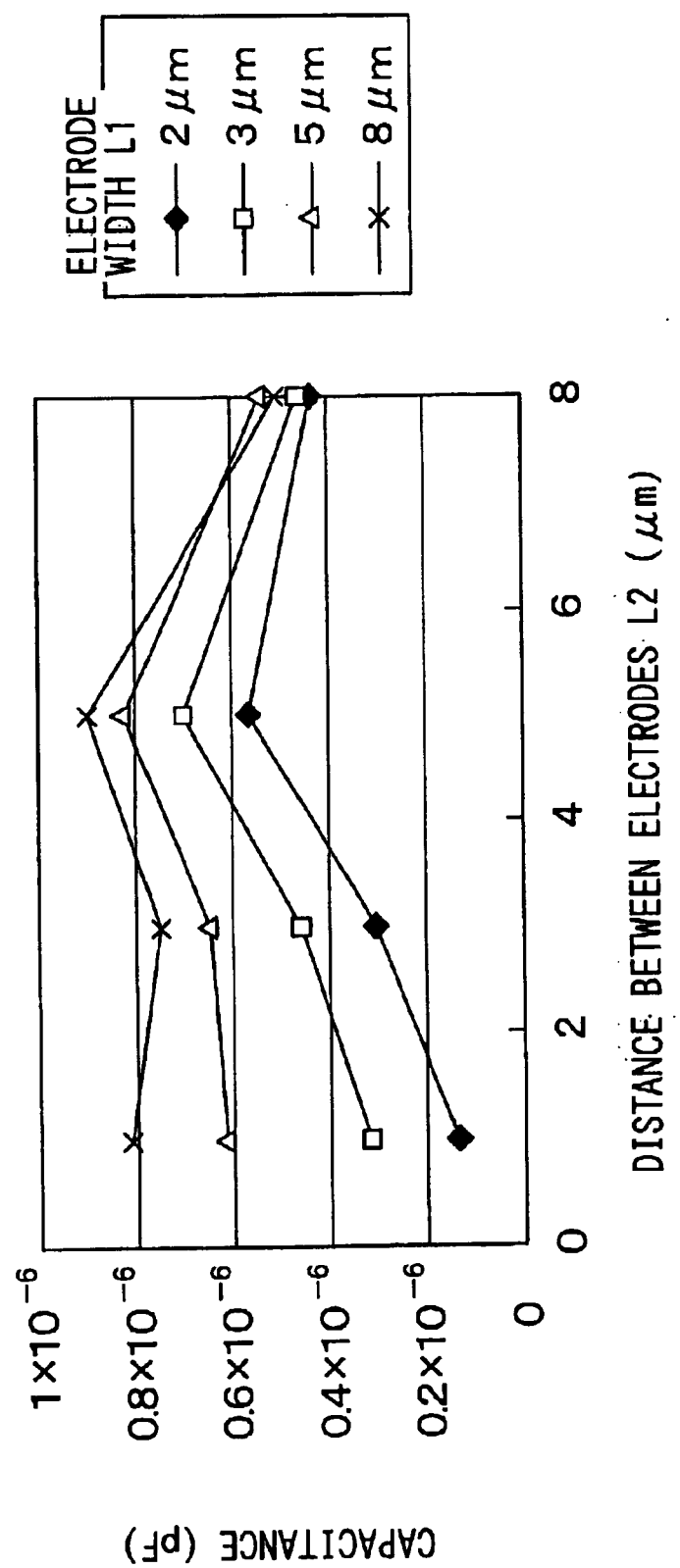
FIG. 3 is a graph showing the relationship between electrode separation distance L2 and changes in capacitance for various electrode widths L1.

FIG. 3 shows a relationship between the distance L2 and the resulting changes in the capacitance with respect to various values of the distance L1. When the humidity-sensitive film 50 is made of polyimide, the width L1 ranges between 2 μm and 8 μm, and the distance L2 ranges from 1 μm to 8 μm.

In FIG. 3, the distance L2 is plotted on the X-axis, and capacitance is plotted on the Y-axis. Black squares represent data for a width L1 of 2 μm, white squares represent data for a width L1 of 3 μm, white triangles represent data for a width L1 of 5 μm, and crosses represent data for a width L1 of 8 μm.

The changes in the capacitance shown in FIG. 3 are for a unit of area K shown in FIG. 1. More specifically, the area K in FIG. 1 includes opposing teeth of the electrodes 31, 32 along a length L3 of 1 μm. Changes in the capacitance were obtained in the area K when humidity ranged between 0% and 100% relative humidity.

FIG. 3 shows that the changes in capacitance are maximized when the distance L2 is 5 μm, regardless of the width L1. In other words, as far as the distance L2 is concerned, the optimum length is 5 μm to most effectively achieve the required changes in capacitance.

However, the results in FIG. 3 alone suggest that the size of the area across which the pair of electrodes 31, 32 face one another could be increased by increasing the number of teeth, or by reducing the width L1, when the spacing L2 is less than 5 μm. As a result, the required change in the capacitance would be achieved without changing the area of the electrodes on the substrate 10. Therefore, the required sizes of the areas for the electrodes 31, 32 for achieving the required change in capacitance was examined at various values for the width L1 and the distance L2. The results are shown in FIG. 4.

Figure 4:
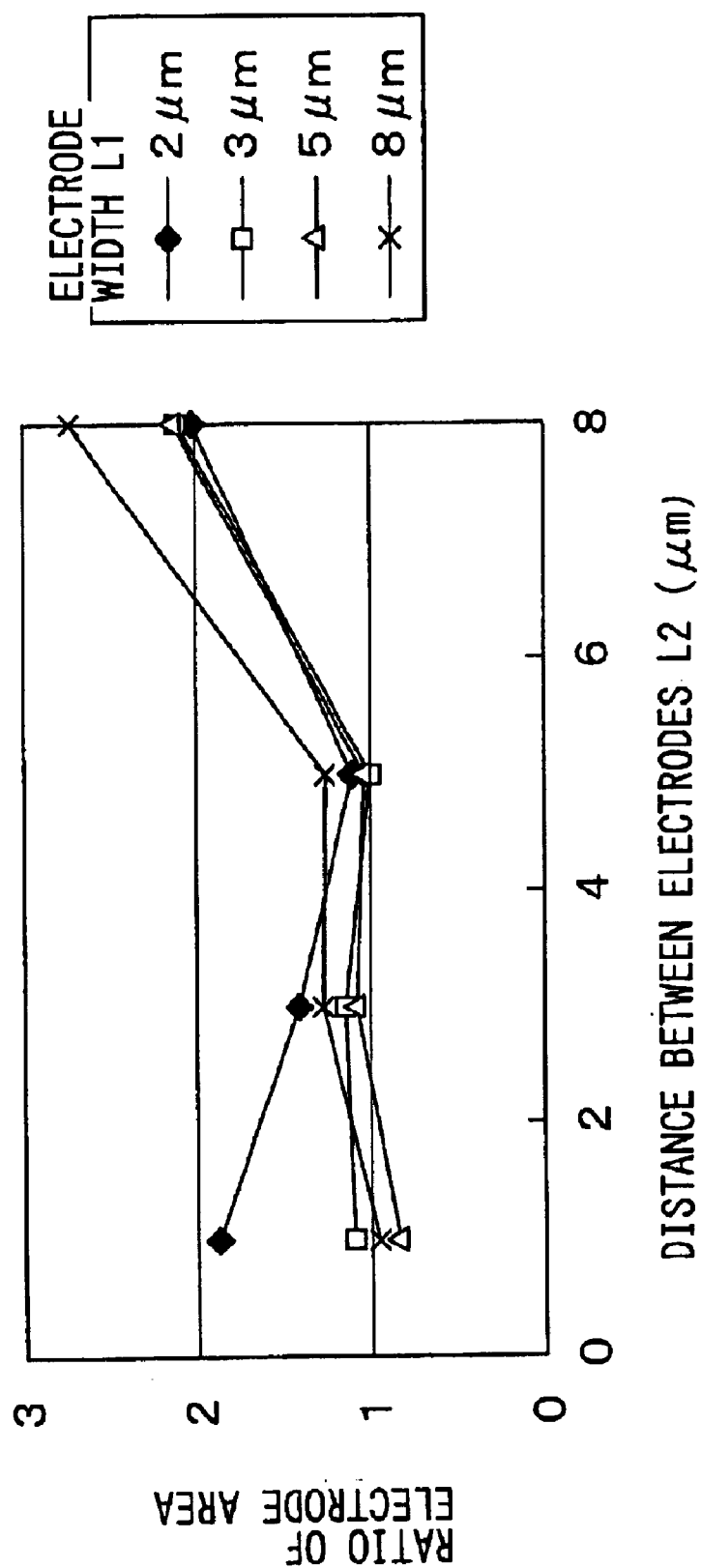
FIG. 4 is a graph showing the relationship between distance electrode separation distance L2 and required electrode area for various electrode widths L1.
Figure 5:
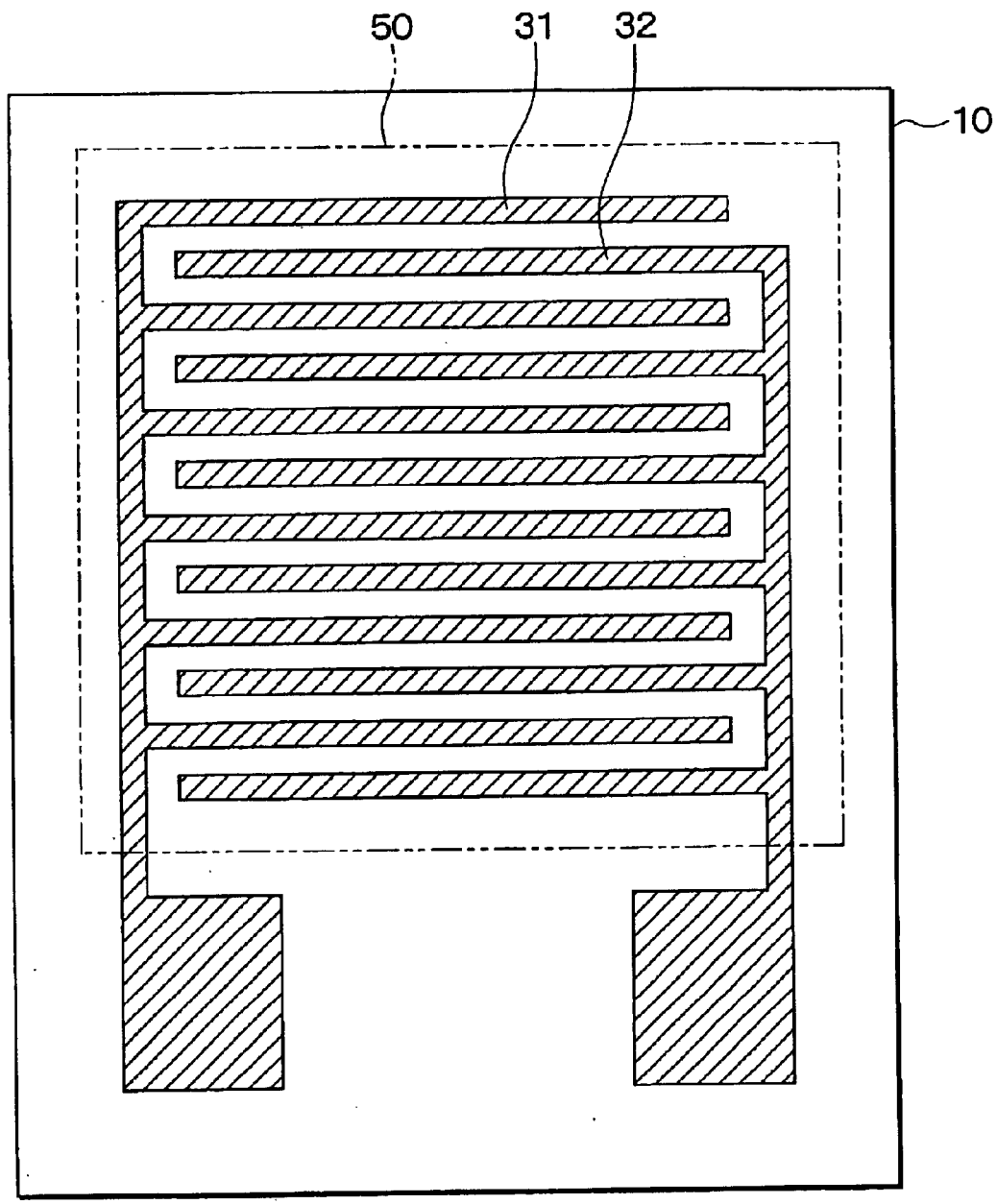
FIG. 5 is a plan view of another capacitive humidity sensor developed by the inventors, for comparison.

FIG. 4 shows a relationship between the distance L2 and the required footprint for the electrodes 31, 32 with respect to various values for the width L1, when the humidity-sensitive film 50 is made of polyimide, the width L1 ranges between 2 μm and 8 μm, and the distance L2 ranges between 1 μm and 8 μm.

In this figure, the area for the electrodes 31, 32 is the size of an area R, surrounded by dotted lines in FIG. 1, or the surface area of the electrode area R. The data have been normalized with the required size of the electrode area R being 1 for achieving the required change in the capacitance of 0.04 pF, when the width L1 is 3 μm and the distance L2 is 5 μm.

FIG. 4 shows the ratio between the electrode area R for required to obtain a change in the capacitance of 0.04 pF and the normalized area for various values for L1 and L2. The smaller the ratio is, the smaller the area occupied by the electrodes 31, 32 on the substrate 10.

In FIG. 4, the distance L2 is plotted on the x-axis, and the surface area ratio is plotted on the Y axis. Black squares represent data for a width L1 of 2 $\mu$m, white squares represent data for a width L1 of 3 $\mu$m, white triangles represent data for a width L1 of 5 $\mu$m, and crosses represent data for a width L1 of 8 $\mu$m.

As shown in FIG. 4, when the width L1 is 2 $\mu$m, and the distance L2 is 5 $\mu$m, the area required on the substrate for achieving the required changes in the capacitance is minimized. Furthermore, the substrate surface areas required for achieving the required changes in the capacitance are almost identical when the width L1 is 3 $\mu$m or larger and the distance L2 is 5 $\mu$m or smaller.

The results shown in FIG. 3 and FIG. 4 demonstrate that, in order to achieve maximum changes in the capacitance at the minimum substrate area, L2 should be 5 $\mu$m when L1 is less than 3 $\mu$m, and L2 should be less than or equal to 5 $\mu$m when L1 is greater than or equal to 3 $\mu$m. As long as these relationships are met, the required changes in the capacitance can be achieved efficiently while minimizing the size of the substrate 10.

Studies by the inventors show that the relationships between the width L1 and the distance L2 described above hold regardless of the thickness of and the materials used for the humidity-sensitive film 50, the electrodes 31, 32, the insulating film 20, and the passivation film 40.

Furthermore, according to the relationships described above, L2<5 $\mu$m when L1>3 $\mu$m, suggesting that, as shown, for example, in FIG. 4, the substrate area for the width L1 at 3 $\mu$m and the distance L2 is 1 $\mu$m would be the same as the substrate area for the width L1 at 5 $\mu$m and the distance L2 at 1 $\mu$m.

In other words, a processing technology with a 5 $\mu$m feature size would achieve the same magnitude of changes in the capacitance at the same substrate area as a finer processing technology with a 2–3 $\mu$m feature size, contributing to manufacturing cost savings.

What is claimed is:

1. A capacitive humidity sensor comprising:

a substrate (10);

a pair of opposed electrodes (31, 32), which are formed on a surface of the substrate (10) in the same plane in isolation from each other, wherein the electrodes are each comb-shaped and have teeth, and the teeth of the electrodes have a generally uniform width (L1) and are interdigitated, and the teeth of one of the electrodes are spaced apart from the teeth of the other electrode by a generally uniform separation distance (L2), and the separation distance (L2) is 5 $\mu$m when the width (L1) is less than 3 $\mu$m, and the separation distance (L2) is less than or equal to 5 $\mu$m when the width (L1) is greater than or equal to 3 $\mu$m; and a humidity-sensitive film (50), the capacitance of which changes with humidity, wherein the humidity-sensitive film covers the electrodes and an area between the electrodes, and humidity is detected based on changes in the capacitance between the electrodes in response to the changes in the humidity of surrounding air.

* * * * *